United States Patent [19]

Haber et al.

[11] Patent Number: 4,890,765
[45] Date of Patent: Jan. 2, 1990

[54] STORAGE CONTAINER FOR BLOOD COLLECTION DEVICES

[75] Inventors: Terry M. Haber; Clark B. Foster, both of El Toro, Calif.

[73] Assignee: Habley Medical Technology Corp., Laguna Hills, Calif.

[21] Appl. No.: 141,018

[22] Filed: Jan. 5, 1988

[51] Int. Cl.⁴ .......................... B65H 3/00; B65H 5/28
[52] U.S. Cl. ........................................ 221/25; 221/73; 221/76; 221/89; 221/102; 221/195; 206/363; 220/403
[58] Field of Search .................... 221/73, 77, 89, 102, 221/195, 69, 76, 210, 311, 25; 206/570, 571, 366, 363; 220/403

[56] References Cited

U.S. PATENT DOCUMENTS 3,941,244  3/1976  Braginetz .......................... 221/102
4,114,780  9/1978  Sharon ............................... 221/102

Primary Examiner—Kevin P. Shaver
Assistant Examiner—Mona Beegle
Attorney, Agent, or Firm—Townsend and Townsend

[57] ABSTRACT

A packaging device for storing, dispensing and collecting a plurality of blood collection units. The packaging device includes a rectangularly shaped container, a first opening for dispensing unused blood collection units and a second opening for receiving the blood collection units after use. The device includes a slidable tape positioned on the upper surface of the container which is in the form of a continuous band mounted on the container. The unused blood collection units are attached to the slidable tape within the container and movement of the slidable tape with respect to the container advances the unused blood collection units into the first opening so that they are then removed from the slidable tape. A bag being initially folded and disposed within the portion of the container for holding the unused blood collection units, the ends of the bag having an open end attached to the container in alignment with a second opening for receiving and holding used blood collection units. Used blood collection units are inserted into the second opening through a door and into the bag, which segregates the used and unused blood collection units in order to prevent contamination of the units to be dispensed. Advancing the unused blood collection units by the slidable tape simultaneously advances all of the unused blood collection, units to thereby provide space for insertion of a used blood collection unit through the second opening and into the bag.

30 Claims, 1 Drawing Sheet

STORAGE CONTAINER FOR BLOOD COLLECTION DEVICES

BACKGROUND OF THE INVENTION

Human blood samples are routinely collected by inserting a needle into a vein and drawing the blood through the needle into a collection vessel. This procedure is currently performed with a needle cannula having two sharp ends, mounting the needle in a generally cup-shaped holder, and placing a pre-evacuated collection tube into the holder so that the proximal needle end pierces the flexible rubber stopper of the tube. As soon as the proximal needle end emerges into the tube the vacuum therein draws blood from the vein, through the needle cannula into the tube. When sufficient blood has been collected the pre-evacuated tube is withdrawn from the needle. If necessary, one or more additional collection tubes are inserted in the holder and pierced by the needle cannual. After the desired number of samples has been collected in this manner the needle is withdrawn from the vein and is disposed of.

This disposal process has the drawback that the used cannula must be considered to be biologically contaminated. Thus, if the person manipulating the contaminated needle accidentally pierces his or her skin with it, infectious diseases may be transmitted. This has become a serious concern since the isolation of the AIDS virus which can and, in fact, has been communicated in this manner. To lessen the likelihood of such contamination, the assignee of this application has developed a disposable blood collection tube holder which forms the subject matter of a copending patent application U.S. Ser. No. 141,019. Briefly, such a holder distinguishes itself from prior art in that it includes a typically cylindrical, outer protective tube which exposes the needle cannula while blood is drawn and is then axially extended over and around the needle cannula to encapsulate it and make it highly unlikely to come into accidental contact with the distal needle tip. Accidental strikes with used needle cannula are thereby prevented. Protective blood collection tube holders of this type are single use devices which are discarded after use.

A medical laboratory may use several hundred of such disposable blood collection tube holders per day. After they have been used they constitute a potentially hazardous contaminated garbage volume which must be disposed of. Due to the relatively large number of single use holders used by such labs and hospitals on a daily basis, this constitutes a relatively large volume of waste. Those used holders which have come in contact with contaminated blood additionally constitute a biological hazard until they are safely disposed of, e.g., incinerated. Although medical laboratories are required to maintain special receptacles for hazardous waste, the receptacles are often at a location remote from where the holder is actually used, i.e., where blood is being drawn. Thus, the technician must either carry the contaminated holder to the receptacle, which in and of itself constitutes an additional hazard, or the holders are improperly disposed of, e.g., by tossing them into the closest waste paper basket. This, in turn, may lead to a further improper handling and disposal of the holder and again constitutes a hazard.

Further, the introduction of disposable holders creates a significant amount of additional contaminated waste volume. In the past a single holder was reused (with fresh needles) as many as two hundred times. Thus, the disposable holder may cause an increase in the accumulating waste volume of as much as two hundred times over what it was in the past. If this increased volume of holders is randomly placed into receptacles, they occupy so much volume that this may inhibit the wide spread use of disposable holders. It is a purpose of the present invention to minimize the volume of this additional waste to thereby promote the orderly and convenient use of such disposable blood collection tube holders.

SUMMARY OF THE INVENTION

The present invention provides a container which simultaneously serves as a package for fresh, unused blood collection tube holders of the type described above and as a disposal receptacle for used and potentially contaminated holders. It physically segregates the two and provides an impermeable seal or membrane as well as a physical spacing rod between them so that used holders cannot come in contact with and, therefore cannot contaminate the fresh holders. The membrane prevents aerosol contamination while the spacer prevents contamination by direct contact.

The container preferably has a rectilinear exterior configuration so that many containers can be stacked, one on top of and one beside the others, in a volume-efficient stacking manner. Further, the interior of the containers is constructed so that the used and unused blood collection tube holders are efficiently packed in a single file, one adjacent to but not in contact with the other to minimize the volume occupied by the holders and the containers, during storage, dispensing and after use.

In a preferred embodiment of the invention the container includes means for conveniently attaching it to an upright wall, such as the side walls commonly found on phlebotomist's trays. This assures that both the dispensing container and the waste receptacle for used holders are always at the point of use. Consequently, the laboratory technician is motivated to dispose of contaminated blood collection tube holders properly, that is by inserting them into the container rather than tossing them into the nearest receptacle, or attempting to resheath the needle cannula as was common in the past, where they would constitute a biological hazard.

Even though the use of disposable blood collection tube holders increases the volume of trash by a large factor, as compared to prior art practices where only the needles were disposed of and the holders were re-used until they were worn out, the additional trash volume is minimized because the used holders are as efficiently packed in the containers as the fresh holders. Moreover, the space-efficient rectilinear exterior shape of the containers promotes the space-efficient stacking thereof after they are filled with used holders. The drawback of a greatly increased inefficiently-packed trash volume, which exists if bulky items such as blood collection tube holders, especially with outwardly movable needle protectors, are randomly disposed of, e.g., by tossing them into a Sharp's container, receptacle or trash bag, is thereby greatly reduced. Thus, the present invention does not significantly increase the trash handling and disposal process. Yet, it securely segregates unused holders from used holders, thereby preventing both aerosol and direct contact contamination, and it assures that the holders are both available where they are used and that they will be properly disposed of after use because the source of fresh holders also constitutes the receptacle for the safe and efficient disposal of used holders.

Turning now to the construction of a packaging device of the present invention, it comprises a preferably rectilinearly shaped container which, on the interior, defines a cavity shaped to receive a supply of, e.g., twenty blood collection tube holders. The container includes a first, dispensing opening adjacent one end thereof which is shaped so that fresh blood collection tube holders can be removed from the container through the opening. A ramp on the interior of the container is preferably shaped so that it engages the fresh holder as it is moved towards the opening and at least partially tilts it out of the opening to facilitate its easy and convenient removal therefrom by the health care worker or laboratory technician.

An elongated, preferably endless tape extends through appropriate slots in an upper wall of the container so that an exterior strand of the tape can be manually engaged and moved longitudinally while an interior strand of the tape engages the fresh holders packaged within the container, by means of adhesive or mechanical connectors such as holder engaging buttons.

The container further includes a second, disposal receptacle opening at an end of the container opposite from the first opening. Contaminated holders are safely inserted and disposed into this second opening. A bag, preferably constructed of a flexible yet impenetrable plastic material or a cloth-reinforced membrane eliminating the possibility of puncture or rupture, is initially folded against one side wall of the container on the interior thereof and has its open end applied to the container so that it communicates with the disposal opening. When the container is filled with fresh blood collection tube holders, the holders retain the bag folded against the container side wall. As fresh holders are dispensed, the last holder in the cavity is moved incrementally away from adjacent the disposal opening, in turn moving the separator (or segregated rod) and thereby vacating space into which the folded bag can expand. When a used holder is inserted through the disposal opening, and displaces the separating rod, it effectively expands the bag. Each additional used holder pushes the ones previously placed into the bag further towards the dispensing opening and into the interior container space being vacated by the fresh holders as they are dispensed.

The disposal opening is further preferably fitted with a one-way door through which used holders are readily inserted into the container. The door is constructed so that used holders cannot be removed from the container and cannot accidentally fall out of it. The closed end of the bag on the interior of the cavity prevents the discharge of used holders through the dispensing opening.

As the foregoing demonstrates, the present invention provides a shipping package and dispensing means for disposable blood collection tube holders which is compact, easily dispensed, easy to use, available as a convenient receptable for the disposal of used holders, and always present and available at the place where the holders are being used. This greatly decreases the likelihood that a technician would improperly dispose of used holders and thereby create a hazard to the technician and others. Further, the provision of the reinforced interior bag safely segregates the used holders from the fresh holders so that the former cannot contaminate the latter during storage by either aerosol or direct contact means.

DESCRIPTION OF THE PREFERRED EMBODIMENTS

Figure 1:
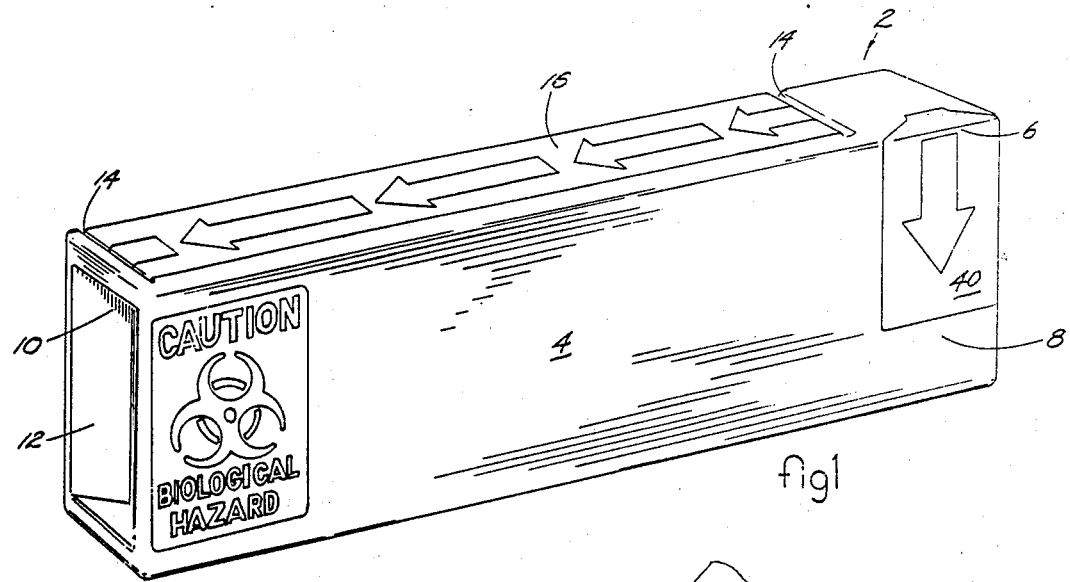
FIG. 1 is a perspective view of a packaging device constructed in accordance with the present invention prior to dispensing of the first unit to be dispensed.
Figure 2:
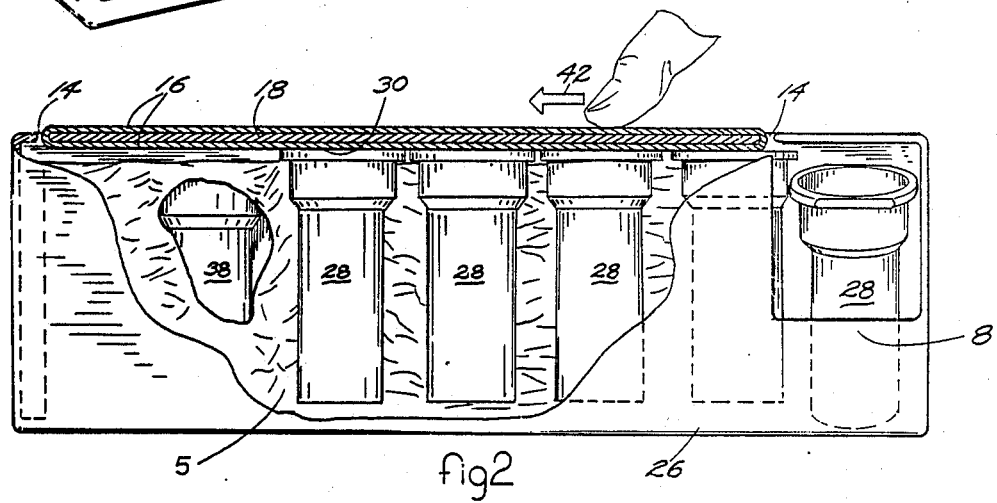
FIG. 2 is a side elevational view, partially in section, of the device, containing both used and unused units.
Figure 3:
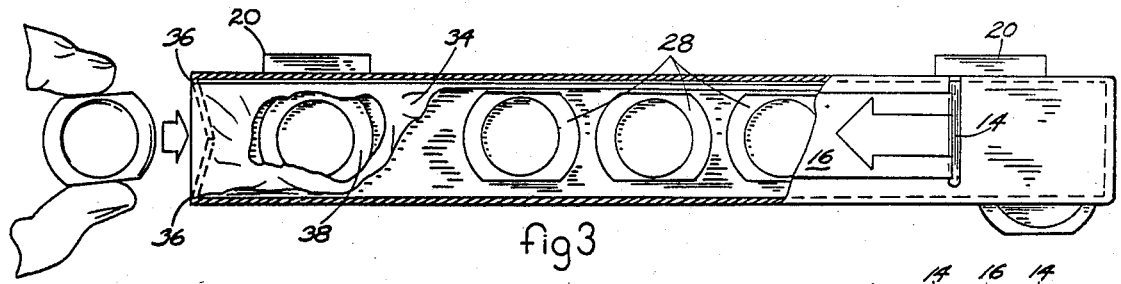
FIG. 3 is a top view, partially in section, of a used unit being inserted into the device.
Figure 4:
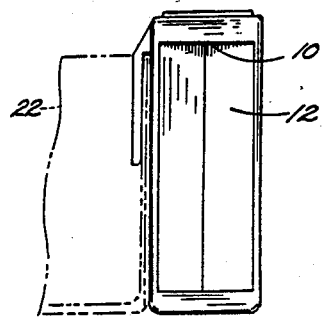
FIG. 4 is a perspective view of the disposal end of the packaging device shown attached to a phlebotomist's blood sample tray.
Figure 5:
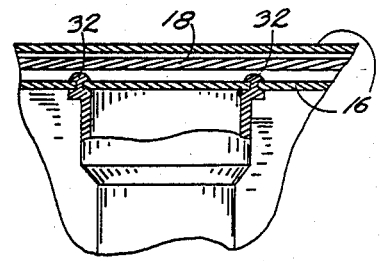
FIG. 5 is a cross-sectional view of an unused unit being attached to the device in an alternate manner.

Referring now to FIG. 1, a packaging device 2 constructed in accordance with the present invention generally comprises a rectangularly-shaped container 4, i.e., a container with a rectilinear exterior outline. On the interior as shown in FIG. 2 the container defines a rectilinear cavity 5 which holds a supply of, say, twenty disposable blood collection tube holders 28. Hooks 20 are attached to container 4 on a rear surface opposite a dispensing opening 6 for attaching the device conveniently within easy reach, for example, to a blood sample tray 22. Dispensing opening 6 is positioned at one end of container 4 above a lip 8, communicates the cavity with the exterior of the container, and is shaped so that blood collection tube holder 28 (or whatever other unit may be stored in the container) can be easily withdrawn from the container. A second opening 10 is positioned at the opposite end of container 4 from dispensing opening 6. It is formed so that used blood collection tube holders 28 can be placed into cavity 5 to thereby safely dispose of them. A one-way door 12 defined by two inwardly angled, hingeably mounted flaps 36 is positioned in second opening 10. The flaps can be opened by pushing them inward, for example when placing a used holder into the container, but they resist opening outwardly which prevents the removal of the used holders through the one-way door. An upper wall 18 of container 4 includes a slot 14 at each end of the container, their function to be described below. As seen most clearly in FIG. 2, a slidable tape 16 comprises a continuous band mounted on the upper wall 18 of the container which extends through slots 14 such that a portion of slidable tape 16 constitutes an exterior strand outside of container 4 and another portion of slidable tape 16 defines an interior strand on the inside of the container. Unused blood collection tube holders 28 are initially attached to the interior strand of the tape 16 within the interior of container 4 by adhesive 30 as shown in FIG. 2, or alternatively by buttons 32 as shown in FIG. 5. The buttons extend through appropriate holes in the tape and they are constructed so that they can be readily withdrawn therefrom to free the holder from the tape. The exterior strand of slidable tape 16 can be manually engaged by the finger of a health care worker to advance the tape longitudinally toward second disposal opening 10, while advancing the interior of tape 16 toward dispensing opening 6.

Unused containers 28 attached to the interior of tape 16 are, thus, advanced toward dispensing opening 6.

Figure 6:
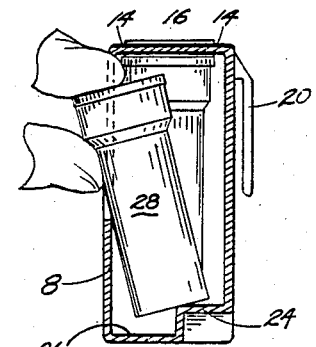
FIG. 6 is an end elevational view in cross-section illustrating an unused unit being dispensed by and removed from the device.

Referring now to FIG. 6, a ramp 24 is formed on floor 26 of container 4. Dispensing opening 6 is positioned in front of and above ramp 24. Ramp 24 is shaped so that it engages a portion of the bottom of the next unused unit 28 to be dispensed as it moves toward dispensing opening 6 and at least partially tilts it out of the opening to facilitate its removal therefrom by the health care worker. Lip 8 extends from floor 26 to the lower edge of opening 6 to retain the next unused unit 28 to be dispensed within container 4, while still allowing it to tilt out of opening 6.

The open end of a bag 34 is attached to the container so that the disposal opening 10 communicates with the inside of the bag and used blood collection tube holders 38 can be placed into the bag through one-way door 12. One-way door 12 permits the used units to be inserted into the container, while preventing their subsequent removal. The bag 34 is initially collapsed into a flat state within the portion of the interior of container 4 for holding unused units 28 and it preferably rests flat against one of the side walls of the container. The unused holders in the container maintain the folded bag in this position. When an unused unit 28 is advanced by sliding tape 16, the last unused unit 28 within the interior of container 4 is moved incrementally away from second disposal opening 10, thereby vacating space into which folded bag 34 can expand.

In operation, referring particularly to FIG. 2, unused blood collection tube holders 28 are initially attached to slidable tape 16 within the interior of container 4. A closure 40, which may be partially adhesive tape, for example, covers dispensing opening 6 during shipment and prior to use. To open the packaging device 2, closure 40 is peeled from dispensing opening 6. In order to dispense an unused blood collection tube holder 28, a health care worker moves slidable tape 16 in the direction of arrow 42. In so doing, all of the unused blood collection tube holders 28 attached to slidable tape 16 are advanced towards dispensing opening 6. The single unused blood collection unit closest to dispensing opening 6 is, thereby, peeled from the tape. As the holder is removed toward the dispensing opening it travels onto ramp 24 and the holder is thereby tilted outwardly into dispensing opening 6. Lip 8 of container 4 prevents contamination from the holder accidentally falling out of the dispensing opening. The lip retains the holder within the interior of the container until it is manually removed by the health care worker.

Inner bag 34 is initially in a collapsed position folded and disposed within the interior of container 4 which holds unused blood collection units 28. As the fresh blood collection tube holders 28 are advanced by moving slidable tape 16, an additional space is provided adjacent second opening 10 for receiving a used blood collection tube holder 38, as seen in FIG. 2, and safely storing it until ultimate disposal of the entire packaging assembly. The container of the present invention constitutes a safe receptacle for the used holders that is always available and easily accessible. The used blood collection tube holder 38 is inserted into second disposal opening 10, through one-way door 12 and into bag 34 which, though initially collapsed, is expanded by the entering holder. The bag is preferably constructed of a liquid and gas impervious material with tensile-reinforced webbing, such as any one of the many available plastic sheets which are currently in wide use as a penetration-resistant nonpermeable packaging material and as a material from which non-leaking bags are made.

After the last fresh blood collection tube holder 38 has been dispersed from container 4 and used, it is inserted through disposal opening 10 into bag 34. The closed end of the bag prevents any of the used holders therein from falling out of or being removed from the containers through dispensing opening 6. While the container holds both fresh and unused holders, the impervious bag safely segregates the two and prevents the used holders from contaminating the fresh ones by either direct contact or aerosol communication.

Container 4 is used for storing and dispensing, unused blood collection tube holders and receiving, disposing of and containing used blood collection tube holders. Inner bag 34 segregates unused blood collection tube holders 28 from used blood collection tube holders 38 and prevents contamination of unused blood collection tube holders 28.

Modifications and variations can be made to the disclosed embodiments without departing from the present invention. However, the process of "inversion," or "male" to "female" transposition, of any elements of the present invention (for example wherein the segregating bag covers the unused blood collection tube holders rather than the contaminated ones, or the blood collection tube holder holding buttons are positioned on the tape rather than the blood collection tube holder itself, or wherein the hard outer shell of the package is transposed to rest within the flexible membrane rather than around it, are equivalent uses of the present invention. The invention is limited only by the following claims.

We claim:

1. A packaging device for storing, dispensing and disposing units, said packaging device comprising a container adapted to hold the units, means for dispensing a single unused unit at a time, means for receiving and holding said unit after use in said container, and means for segregating and preventing contamination of the unused units from the used units, said means for segregating forming an impermeable physical barrier between said means for dispensing unused units and said means for receiving and holding said unit.

2. The packaging device as defined by claim 1, wherein said means for dispensing comprises an opening in the container.

3. The packaging device as defined by claim 1, wherein said means for dispensing comprises an opening and a surface formed in the container, said surface being shaped and positioned in the container to engage a portion of an unused unit and urge it into said opening as the unit is moved towards the opening.

4. The packaging device as defined by claim 3 wherein said surface is formed integrally with said container.

5. The packaging device as defined by claim 1 further including means for advancing an unused unit to said means for dispensing.

6. The packaging device as defined by claim 1, wherein said means for segregating the unused and used units comprises a sheet separating said unused and used units and preventing the contamination of said unused units by the used units.

7. The packaging device as defined by claim 1 further including gate means for preventing a used unit from being removed from said container.

8. The packaging device as defined by claim 1, wherein said units to be packaged comprise sterilized units.

9. The packaging device as defined by claim 1, wherein said container has a rectilinear exterior shape.

10. The packaging device as defined by claim 1 wherein said means for dispensing comprises means manually engageable from the exterior of said container, and extending into the container, each unused unit being removably attached to said means for dispensing.

11. The packaging device as defined by claim 1, wherein said means for segregating the unused and used units comprises a bag separating said unused and used units and preventing the contamination of said unused units by the used units.

12. The packaging device as defined by claim 1 wherein said means for dispensing comprises means for misaligning the unused unit to be dispensed from the remaining unused units.

13. The packaging device as defined by claim 1 further including means for advancing an unused unit to said means for dispensing, said means for advancing being independent of said means for receiving and holding said unit after use.

14. A packaging device for storing, dispensing and disposing units, said packaging device comprising a container adapted to hold the units, a longitudinally movable tape mounted to the container for dispensing a single unused unit at a time, the tape being manually engageable from the exterior of said container, and extending into the container, each unused unit being removably attached to said tape, means for receiving and holding said unit after use is said container, and means for segregating the unused units from the used units so as to prevent contamination of said unused units by the used units.

15. The packaging device as defined by claim 14, wherein each unused unit is removably attached to said tape by adhesive.

16. The packaging device as defined by claim 14, wherein each unused unit is removably attached to said tape by a button.

17. A packaging device for storing, dispensing and disposing units, said packaging device comprising a container adapted to hold the units, means for dispensing a single unused unit at a time, means for receiving and holding said units after use in said container, a bag positioned within said container in a collapsed state when said container is filled with unused units for separating and segregating the unused units from the used units so as to prevent contamination of said unused units by the used units.

18. A packaging device for storing, dispensing and disposing units, said packaging device comprising a container adapted to hold the units, means for dispensing a single unused unit at a time and means for receiving and holding said unit after use in said container, means for segregating the unused units from the used units so as to prevent contamination of said unused units by the used units, and a one-way door for permitting a used unit to be received in the container and preventing a used unit in the container from being removed from said container.

19. A packaging device for blood collection units for storing the units, dispensing them at a point of use, and for holding used units for subsequent disposal in a manner which prevents the contamination of the unused units by the used units, said device comprising:
a container defining a cavity adapted to hold a plurality of units in a single file;
means for dispensing a single blood collection unit at a time from said container, said dispensing means including:
an opening in said container;
a ramp positioned adjacent a floor of said container for urging unused blood collection units out of said opening when the unit is moved toward the opening;
an elongated tape positioned adjacent an upper wall of said container having a first portion accessible from the exterior of the container and a second portion engaging the unused unit to be dispensed for advancing the unused blood collection units onto said ramp by longitudinally moving the first portion of the tape;
means for disposing of a used blood collection unit in said container, said disposing means including:
a second opening in said container for inserting used blood collection units into said container;
a door in said opening for maintaining used blood collection units in said container; and
an impervious bag positioned in said container and communicating with the second opening for receiving said used blood collection units, wherein said used blood collection units are inserted into said bag through said door and are thereby segregated from said unused blood collection units to prevent contamination of said blood collection units to be dispensed.

20. The packaging device as defined by claim 19 wherein said door is a one-way door permitting insertion of said used blood collection units into said container and preventing removal of said used blood collection units from said container after insertion.

21. The packaging device as defined by claim 19 wherein said bag is in a collapsed state within said container and spaced apart from at least one wall of the container when only unused blood collection units are within said container.

22. The packaging device as defined by claim 19 wherein said unused blood collection units are removably attached to said tape.

23. The packaging device as defined by claim 22 wherein said unused blood collection units are attached to said tape by adhesive means.

24. The packaging device as defined by claim 22 wherein said unused blood collection units are attached to said tape by buttons.

25. The packaging device as defined by claim 19 wherein said tape is a continuous band mounted to said upper wall and having a portion of a first strand disposed exteriorly and a second strand disposed interiorly of the container, said unused blood collection units being attached to said first strand of the tape within said container and said band may be moved with respect to said container from the exterior thereof so as to move an unused blood collection unit attached to the second strand towards the first opening.

26. The packaging device as defined by claim 25, wherein said container further comprises slots positioned in the upper wall of said container and portions of said continuous band between the first and second strands extend through the slots.

27. The packaging device as defined by claim 19, wherein said container has a rectilinear exterior configuration to facilitate the stacking of multiple containers.

28. A packaging device for blood collection units comprising:

- a container including means for dispensing a single fresh blood collection unit at a time and means for holding and receiving said used units after use, a portion of the interior of said container holding a plurality of fresh blood collection units to be dispensed;
- said means for dispensing including a dispensing opening in said container through which fresh units can be removed from the container;
- said means for holding and receiving including:
  - a disposal opening in said container for inserting used blood collection units into said container;
  - a receptacle within said container for receiving the used blood collection units and being defined by a bag, said bag being initially folded and disposed within said portion of said container for holding unused blood collection units, said bag having an open end attached to said container and in communication with said disposal opening;
  - an upper wall of said container having slots;
  - a transport mechanism mounted to the upper wall of said container, the transport mechanism being manually actuable from the exterior of the container, extending through the slots into the interior of the container and releasably engaging the fresh blood collection units in the container for advancing them simultaneously from the interior of the container towards the dispensing opening when the mechanism is actuated, whereby advancing of said fresh blood collection units provides space for insertion of a used blood collection unit into said disposal opening and insertion of a used blood collection unit expands said bag to receive and hold said used blood collection unit.

29. The packaging device as defined by claim 28 wherein said transport mechanism comprises a continuous band including a first portion of said band positioned outside said container and another portion of said band positioned inside said container through said slots.

30. The packaging device as defined by claim 28 further comprising means for preventing removal of said used blood collection units once said units are inserted into said container.

* * * * *